United States Patent [19]
Hauck et al.

[11] Patent Number: 5,330,512
[45] Date of Patent: Jul. 19, 1994

[54] ELECTRODE CHARGE-NEUTRAL SENSING OF EVOKED ECG

[75] Inventors: John A. Hauck; Julio C. Spinelli, both of Shoreview, Minn.

[73] Assignee: Cardiac Pacemakers, Inc., St. Paul, Minn.

[21] Appl. No.: 997,442

[22] Filed: Dec. 28, 1992

[51] Int. Cl.$^5$ .............................................. A61N 1/00
[52] U.S. Cl. ....................................................... 607/28
[58] Field of Search ............................... 607/18, 25–28

[56] References Cited

U.S. PATENT DOCUMENTS

| | | |
|---|---|---|
| 3,924,641 | 12/1975 | Weiss . |
| 4,343,312 | 9/1982 | Cals et al. . |
| 4,373,531 | 2/1983 | Wittkampf et al. . |
| 4,493,327 | 1/1985 | Bergelson et al. ............... 128/731 |
| 4,543,956 | 10/1985 | Herscovic . |
| 4,585,004 | 4/1986 | Brownlee ............................ 607/27 |
| 4,664,116 | 5/1987 | Shaya et al. ........................ 607/27 |
| 4,674,509 | 6/1987 | DeCote, Jr. . |
| 4,686,988 | 9/1987 | Sholder . |
| 4,708,142 | 11/1987 | DeCote, Jr. . |
| 4,817,605 | 4/1989 | Sholder . |
| 4,821,724 | 4/1989 | Whigham et al. . |
| 4,878,497 | 11/1989 | Callaghan et al. . |
| 4,903,700 | 2/1990 | Whigham et al. . |
| 4,922,907 | 5/1990 | Hedin et al. ....................... 607/27 |
| 4,955,376 | 9/1990 | Callaghan et al. . |
| 5,161,529 | 11/1992 | Scotts et al. . |

FOREIGN PATENT DOCUMENTS

| | | |
|---|---|---|
| 0334681 | 9/1989 | European Pat. Off. . |
| 9202274 | 2/1992 | PCT Int'l Appl. . |
| 2193101 | 2/1988 | United Kingdom . |

Primary Examiner—Lee S. Cohen
Assistant Examiner—Marianne Parker
Attorney, Agent, or Firm—Haugen and Nikolai

[57] ABSTRACT

A cardiac pacemaker signal processing circuit adapted to obtain an evoked ECG signal. The circuit senses the electrical signals of the ring and tip electrodes in the unipolar mode from the bipolar lead after the electrical pacing stimulus has been applied to contract the ventricle of the heart. The residual oppositely polarized potentials at the ring and tip electrode, as well as the sensed evoked ECG signals, are added together to cancel out the opposing residual potentials, but to add the common polarized ECG signal. Thus, a high quality evoked ECG signal is obtained, free of the residual potentials, and subsequently utilized by R-wave detection circuits for sensing the QRS complex. The circuit includes compensating signal processing circuits to provide time domain signal processing weighting functions to match exponential time delay of the tip and ring electrodes, and includes amplitude adjusting compensation as well. Thus, the absolute amplitudes of the opposite polarized residual potentials will be adjusted to be equal, are summed, and canceled or nulled at the appropriate time in the time domain. Both biphasic and tripbasic pace pulse techniques are not required, the pace pulse amplitude can be reduced to extend the battery life of the pacemaker. Further, the post pace re-charging cycle is only interrupted and undertaken-passively to, again, reduce current drain on the battery. Classic R-wave detection circuits are adaptable to the signal processing circuit of the present invention.

31 Claims, 2 Drawing Sheets

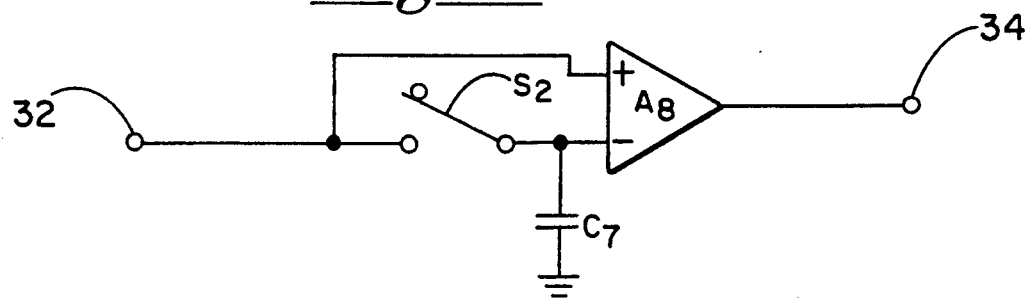
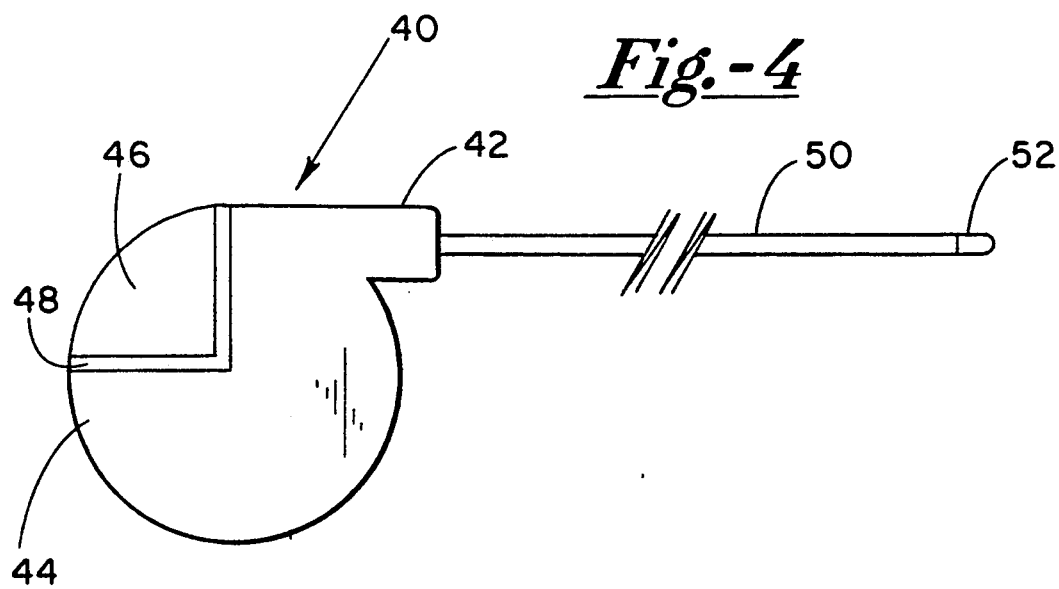

ELECTRODE CHARGE-NEUTRAL SENSING OF EVOKED ECG

BACKGROUND OF THE INVENTION

I. Field of the Invention

This invention relates generally to pacemakers used for Bradyarrhythmia therapy, and more particularly, to control circuitry which may be disposed in the can of the pacemaker to sense the evoked ECG signal from the heart, or disposed in external equipment such as a Pacing System Analyzer.

II. Background of the Invention

Automatic capture is the feature of being able to ascertain whether or not a pace pulse from a pacemaker has in fact evoked a depolarization of the heart ventricle. When the ventricle depolarizes, the heart evokes a QRS complex which can be sensed and processed to verify that the heart depolarized, or to be processed such that therapeutic action by the pacemaker is facilitated. Many prior art approaches have focused upon altering the shape or polarity of the pacing pulse to the pacing electrodes to reduce polarization voltage upon them shortly after the pacing pulse terminates. This technique is known as biphasic or tripbasic pulse generation. Then, evoked response sensing can ensue much the same as normal intrinsic ECG sensing is done. The disadvantages of these approaches are that they end up using more energy than a single pulse, all the while to facilitate a feature of automatic capture-output regulation, which desires to lower device current drain by lowering the output amplitude closer to its minimum, known as the pacing threshold. Further, these approaches do not always adequately overcome the residual polarization on the bipolar electrode leads, which potentially can inhibit and degrade the sensing and analysis of the evoked ECG signal. Typically, potentials of 100 millivolts or more can remain across the bipolar electrodes after a depolarization of the ventricle. In contrast, the normal evoked ECG response can be as low as 5 millivolts. Thus, the ability to sense a low voltage ECG signal by using the bipolar lead electrodes can be difficult when the electrodes remain polarized.

U.S. Pat. No. 4,858,610 to Callaghan et al., teaches an apparatus and method of detection of cardiac evoked potentials. This invention teaches applying a stimulation pulse in a unipolar mode to the tip electrode, wherein the ring electrode is used to sense the evoked ECG signal, also in a unipolar mode. The evoked ECG signal is sensed by the ring electrode during a predetermined window after generation of the pacing pulse. A charge dump circuit is taught for discharging the polarization potential of the tip electrode prior to the window for sensing the evoked ECG signal. Accordingly, signal interference caused by residual polarization of the first electrode is reduced. However, this device still requires biphasic and tripbasic pulse generation, which is more complicated and requires more energy than desired. This technique reduces the useful life of the internal pacemaker battery.

OBJECTS OF THE INVENTION

It is accordingly a principle object of the present invention to provide signal processing circuitry which can be included in an implantable pacemaker, and which facilitates automatic capture detection by sensing the evoked QRS complex from a bipolar pacing lead.

Still yet a further object of the present invention is to provide signal processing circuitry which facilitates automatic capture detection by sensing the evoked QRS complex from a unipolar pacing lead.

Still yet a further object of the present invention is to provide signal processing circuitry which can be included in external devices, such as Pacing System Analyzers, or the like, for obtaining the evoked QRS complex.

It is a further object of the present invention to provide signal processing circuitry which can detect the evoked QRS complex even when a large residual potential remains across the bipolar electrodes.

It is still yet a further object of the present invention to provide signal processing circuitry which does not require biphasic or triphasic pulse generation pacing techniques.

Still yet a further object of the present invention is to provide signal processing circuitry which is sufficiently sensitive to sense the evoked QRS complex such that the amplitude of the stimulus pulse can be reduced, yet be sufficient to evoke a depolarization of the ventricle, to thus extend the life of the pacemaker battery.

SUMMARY OF THE INVENTION

The foregoing features and objects are achieved by providing an implantable pacemaker suited for Bradyarrhythmia therapy which senses and obtains the evoked ECG signal. The invention adds electrical signals obtained from the tip and ring electrode after pace pulse generation, rather than using differential techniques, to cancel out the opposing residual potentials on the electrodes and to add the common potential unipolar ECG signal sensed on both the tip and ring electrode. In a unipolar lead implementation, the can replaces the ring as the anode, and another electrode, such as a small button electrode on the pacemaker header, serves as the indifferent or reference electrode. The invention comprises an apparatus for cardiac pacing and sensing comprising a bipolar cardiac pacing lead adapted for positioning within a heart chamber. The bipolar lead has a first and second electrode on its distal end which are electrically isolated from one another. A reference electrode electrically coupled to body tissues is provided which is electrically isolated from the first and second electrode, and which may comprise the can, or case, of the apparatus. The invention includes a means for transmitting to both the first and second electrode an electrical stimulus pulse in a bipolar mode. A signal processing circuit is connected to both the first, second and reference electrodes for obtaining the evoked ECG electrical signal. The circuit senses a first electrical signal at the first electrode in a unipolar mode in reference to the reference (pacemaker case) electrode, and senses a second electrical signal at the second electrode, also in a unipolar mode and in reference to the reference electrode. The circuit provides a means for adding the first and second signals from the first and second electrodes to cancel out residual opposite polarized potentials to obtain the evoked ECG electrical potential. Since the electrical stimulus pulse is applied in a bipolar mode to the first and second electrodes, by adding the first and second electrical signals, the residual opposite polarized potentials cancel, yet the evoked electrical potential which is sensed by both a first and second electrodes will add. Thus, the low level evoked ECG signal can be readily sensed, and subsequently used for automatic capture verification, or used in any diagnostic or therapeutic action by the pacemaker. Classic R-wave detection circuits for sensing the QRS complex may be suitable for the subsequent signal processing. The above circuit can be implemented in both analog and digital techniques. Thus, the above apparatus has wide application and can be incorporated into a variety of pacemakers, and Pacing System Analyzers, or the like.

In the preferred embodiment, the means for transmitting the electrical stimulus pulse in a bipolar mode to the first and second electrode further has a means for recharging its output in preparation for the next required electrical stimulus pulse. A natural effect of this recharge, which follows the stimulus pulse, is a discharge of the first and second electrodes. The means for transmitting further comprises a means for momentarily interrupting the recharging of the output, typically three milliseconds after pacing. After a suitable sensing window has ended, typically 60 milliseconds after the stimulus pulse, the recharge resumes until the output has fully charged for the next stimulus. The recharging is done passively through the heart ventricle rather than actively using biphasic or triphasic pulse generation, such that the recharge period is longer, but the current drain on the battery is reduced. However, the present invention is suited to be used with active recharging if desired. Upon interrupting the recharging cycle, the ECG signal can be sensed by the circuit after a settling period during an appropriate window, approximately 10 to 60 milliseconds after application of the stimulus pulse. The time after pacing when the recharge cycle is interrupted is selectable and programmable in the pacer electronics by the physician, which is referred to as variable or dynamic recharge interruption. Normalizing may be performed at the start of the sensing window, where a present value can be subtracted from a sensed output value from the circuit. Subsequently, the weighting function can be adjusted or calibrated prior to sensing the evoked ECG signal, if necessary. Thus, a dynamic balancing can be performed immediately prior to obtaining the evoked ECG signal.

Since the ring and tip electrodes normally have different surface areas, geometries, and may be comprised of different materials, both amplitude and time domain adjustments are incorporated into the present invention to further improve the sensing of the evoked ECG signal. A first order model of either electrode is a series resister and capacitor. The values of the tip and ring RC time constants may not be identical due to aforementioned physical differences. Therefore, reactive (e.g. capacitive) compensation of one electrode's signal with respect to the other electrode's signal prior to the summing function, is advantageous to provide time domain adjusting functions. An amplitude adjusting circuit is also provided for adjusting the amplitude of either or both the first and second electrical signals as well. Thus, the first and second electrical signals are sensed on the bipolar electrodes, but in the unipolar mode, and can be normalized prior to obtaining the evoked ECG signal.

In the preferred embodiment, the time domain adjusting circuit is provided in an analog embodiment using an operational amplifier with a variable capacitor tied between the amplifier input and ground. The amplitude adjustment circuit is realized by providing a variable feedback resistor to adjust the gain of the amplifier. However, it is recognized that either digital signal processing or analog sampled data techniques can be utilized as well. For example, an operational amplifier is disclosed having an input switched alternately between the ring and tip electrode using switched capacitor or switched current techniques, for instance, at four kilohertz. The obtained signal can then be processed through a low-pass filter to average the input, which is alternating between the tip and ring electrode, to reject the higher frequency components of the resulting ECG signal, and to cancel the opposite polarized residual potentials. A corner frequency of 100 hertz has been determined to be ideal using this technique.

The analog signal processing techniques of time domain signal processing and amplitude adjustments are not necessary to obtain the evoked ECG signal according to the present invention. Rather, a summation amplifier which sums the signals on the first and second electrodes, namely the ring and tip electrodes, and which are sensed in the unipolar mode, is all that is required.

BRIEF DESCRIPTION OF THE DRAWINGS

FIG. 3 illustrates a classic sample and hold circuit adapted to the outputs of either embodiment shown in FIGS. 1 and 2 to remove any offset prior to threshold detection circuitry; and FIG. 4 illustrates yet another alternative embodiment having a pacemaker can providing both the reference electrode, which is attached to body tissues, and the second isolated electrode, wherein a unipolar lead is implemented to transit a pacing pulse to the remotely located first electrode.

Other objects, features and advantages of the present invention will become apparent to those skilled in the art through the Description of the Preferred Embodiment, Claims, and drawings herein, wherein like numerals represent like elements.

DESCRIPTION OF THE PREFERRED EMBODIMENT

Figure 1:
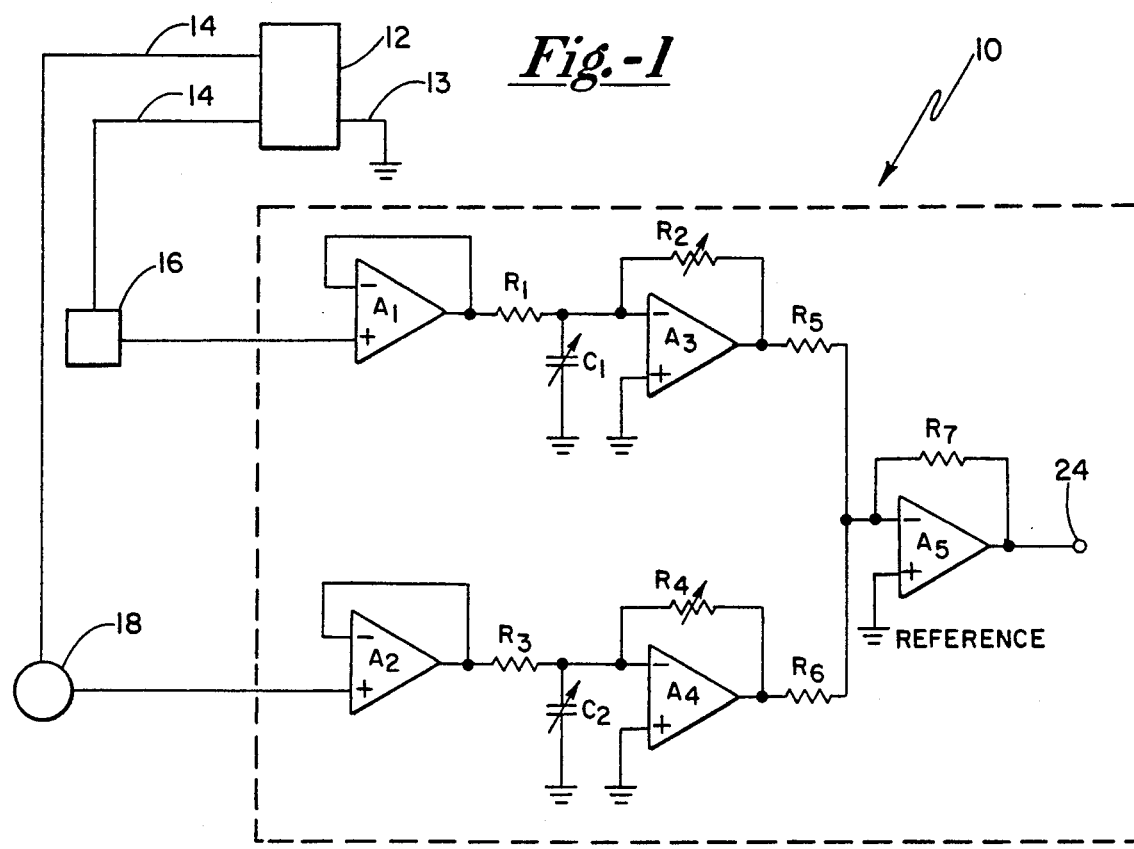
FIG. 1 illustrates a schematic drawing of an analog signal processing circuit according to the preferred embodiment of the invention which is coupled to the ring and tip electrode of a bipolar lead, wherein the circuit can reside in the can of the pacemaker. As shown, the can of the pacemaker serves as the reference electrode and is used as a reference when obtaining ECG signals from the respective electrodes in a unipolar mode.

Referring to FIG. 1, an analog signal processing circuit capable of sensing and obtaining an evoked ECG signal from bipolar pacemaker electrodes is illustrated at 10. Circuit 10 is powered by a battery (not shown) and preferably resides in a pacemaker 12. Pacemaker 12 has a metal can, preferably comprised of titanium, which serves as a grounded reference electrode 13 and is electrically coupled to body tissues. The common of circuit 10, which includes sensing amplifiers, is also coupled to ground reference 13 as will be discussed shortly. A bipolar electrode lead 14 is coupled to internal circuitry in pacemaker 12, and communicates a generated stimulation pace-pulse during the pacing window to a ring electrode 16 and a tip electrode 18 in a bipolar mode. Electrodes 16 and 18 are closely spaced to one another, but are electrically separated to facilitate applying a potential thereacross, and are typically positioned in a heart ventricle.

Circuit 10 resides in can 12 of the pacemaker and is electrically connected to the ring and tip electrode via conductors 14. However, for illustration purposes, FIG. 1 illustrates circuit 10 external to the can 12 and coupled to the tip and ring electrodes. Circuit 10 comprises a first operational amplifier $A_1$ having unity gain for sensing and obtaining electrical signals on ring electrode 16, in a unipolar mode in reference to ground, which is the can of pacemaker 12 and which is electrically coupled to body tissues. This electrical signal includes a composition of residual potential resulting after pacing on the ring electrode and an evoked ECG potential. Similarly, a second operational amplifier $A_2$ having nominal gain is provided for sensing and obtaining electrical signals at tip electrode 18, also in a unipolar mode in reference to the grounded can of pacemaker 12. These signals also include a composition of residual potential resulting after pacing on the tip electrode and on evoked ECG potential. Amplifiers $A_1$ and $A_2$ buffer and subsequently communicate the respective sensed signal via a fixed series resistor $R_1$ and $R_3$, respectively, to a respective signal processing amplifier $A_3$ and $A_4$.

Amplifiers $A_3$ and $A_4$ provide a weighting function, including time domain and amplitude domain weighting. Amplifier $A_3$ includes a variable capacitor $C_1$ connected between the negative input and ground for adjusting the time constant to provide time delay signal processing. By adjusting the value of capacitor $C_1$, the exponential decay characteristic of the sensed signal from the input to the output of amplifier $A_3$ can be selectively controlled. Similarly, a variable capacitor $C_2$ is provided across the input of amplifier $A_4$ and ground to provide time domain signal processing of the electrical signal obtained from the tip 18 electrode. By selectively adjusting the value of either capacitor $C_1$ or $C_2$, the exponential decay of the respectively obtained tip and ring electrical signals can be matched, and as they are of opposite polarity, they will cancel when added together as will be described shortly.

Amplitude signal processing is also provided by the weighting function of amplifiers $A_3$ and $A_4$ using a variable feedback resistor $R_2$ and $R_4$, respectively. By adjusting the value of the respective variable resistors, the gain of the respective amplifiers $A_3$ and $A_4$ are adjusted. Hence, the signal levels provided by the outputs of amplifiers $A_3$ and $A_4$ can be adjusted with respect to one another.

Subsequently, the electrical signals from amplifiers $A_3$ and $A_4$ are routed through respective series resistors $R_5$ and $R_6$, and are then both connected to the negative input of summing amplifier $A_5$. Amplifier $A_5$ sums both of these signals obtained from the ring electrode 16 and tip electrode 18, after they have been appropriately processed in either or both the time domain or in amplitude. The output of amplifier $A_5$ provides nominal gain and has an output signal which can be subsequently diagnosed and used by automatic capture circuits. A feedback resistor $R_7$ is provided across amplifier $A_5$ to adjust the overall gain of amplifier such that the output signal has an amplitude suitable for subsequent processing circuits. Thus, the present invention includes a weighting circuit for providing a dynamic balancing feature to null the residual potentials.

The values of $C_1$, $C_2$, $R_2$ and $R_4$ can be set by the attending physician at the time of implantation, remotely set by suitable pacemaker controlling circuitry accessible by the physician, or adjusted during diagnostic routines. The determination of the weighting function may also be done by pacing in a known refractory period and adjusting the weighting function to achieve a desired null result, referred to as normalizing the circuitry, as will be described shortly. Alternatively, the weighting function may be determined from prior testing, and be applied in the implantable device by a lookup table in the pacer electronics that allows different weights at different pacing amplitudes or pulse widths. Finally, weighting may be dispensed with altogether. That is, $C_1=C_2$, and $R_2=R_4$. In this case, the residual artifact, using the summing technique alone, being on the order of only a few millivolts, may be rejected by subsequent signal processing.

One key feature of circuit 10 according to the present invention is that since residual potentials which exist at both ring electrode 16 and tip electrode 18 post-pacing are opposite in polarity, they will cancel out when added by amplifier $A_5$. However, since the electrical signals obtained at ring electrode 16 and tip electrode 18 are both obtained in the unipolar mode, the sensed evoked ECG signal obtained at both ring electrode 16 and tip electrode 18 have the same polarity, and will be added by amplifier $A_5$. Thus, the present invention adds the signals obtained at the tip and ring electrodes, rather than processing the signals in the differential mode. The present circuit rejects the opposed residual polarization at the tip and ring electrode, by canceling, but sums and outputs the common signal, namely the evoked ECG signal. The rejection of the opposing residual polarization signals may be as high as 60 dB.

The signal processing and weighting function adjustments provided by amplifiers $A_3$ and $A_4$ are important if it is desired to obtain an absolute null of the residual polarization when added. Tip electrodes 16 and ring electrodes 18 usually have different surface areas, geometries, and are comprised of different materials. Thus, the amplitude of the residual potentials are not necessarily equal at electrodes 16 or 18 post pacing. By adjusting the amplitude of the signals processed by amplifiers $A_3$ and $A_4$, the outputted amplitudes can be provided so that they are equal, but opposite, and are cancelled or nulled when added by amplifier $A_5$.

Again, if an absolute null of the polarization voltages is desired after summation, the weighting functions of amplifiers $A_3$ and $A_4$ are also important, since the exponential decay characteristics of the sensed residual potentials at ring electrode 16 and tip electrode 18 can vary. By providing time domain signal processing by adjusting the respective time constant, the decay characteristic of the signals can be adjusted with respect to each other to ensure that, again, when added at amplifier $A_5$, the residual oppositely polarized potentials will cancel. Hence, only the evoked ECG signal is outputted by amplifier $A_5$ to output terminal 24.

It is particularly noted that, theoretically, to practice the present invention and obtain the evoked ECG signal, only amplifier $A_5$ is required to sum the unipolar signals from ring electrode 16 and tip electrode 18 to cancel out, or greatly reduce the polarization artifact. However, particularly if an absolute null is desired, time domain and amplitude adjustments may be required for each sensed electrical signal prior to summation to provide a more effective matching of the opposing polarization potentials. Forward amplifiers $A_1$ and $A_2$ also are not required, but are desirable to provide buffering prior to time domain and amplitude signal adjustments.

The circuit common of signal processing circuit 10 is shown as connected to the pacemaker can, such that unity gain buffers $A_1$ and $A_2$ can recover the unipolar signals from ring and tip electrodes, respectively. An alternative arrangement would not require that the can be tied to circuit common, however. In this alternative, one would use differential amplifiers for $A_1$ and $A_2$. These amplifiers would output a signal proportional to the difference of potential between the can and ring, and the can and tip, respectively, which signals can be subsequently summed as discussed.

It is also noted that while amplifiers $A_1$ and $A_2$ are shown configured as non-inverting buffers, and amplifiers $A_3$, $A_4$ and $A_5$ are shown as inverting amplifiers, they need not be restricted as such. The only requirement is that both amplifiers $A_1$ and $A_2$ invert or are non-inverting amplifiers, and that amplifiers $A_3$ and $A_4$ are either both inverting or non-inverting amplifiers. Finally, amplifier $A_5$ can be configured as inverting or non-inverting since subsequent signal processing of the evoked ECG signal is usually accomplished by absolute value signal processing techniques. Thus, the polarity of the evoked ECG signal at port 24 is not important.

Subsequent signal processing of the evoked ECG signal at port 24 may be processed by classic R-wave detection circuits for sensing the QRS complex. The subsequent signal processing may also be accomplished using sampled data (switched capacitors or switched currents), or digital techniques. Thus, a variety of subsequent signal processing circuits can facilitate automatic detection of the evoked ECG signal. Thus, circuit 10, as shown, is very useful and suitable for a wide variety of existing pacemaker processing circuitry.

Figure 2:
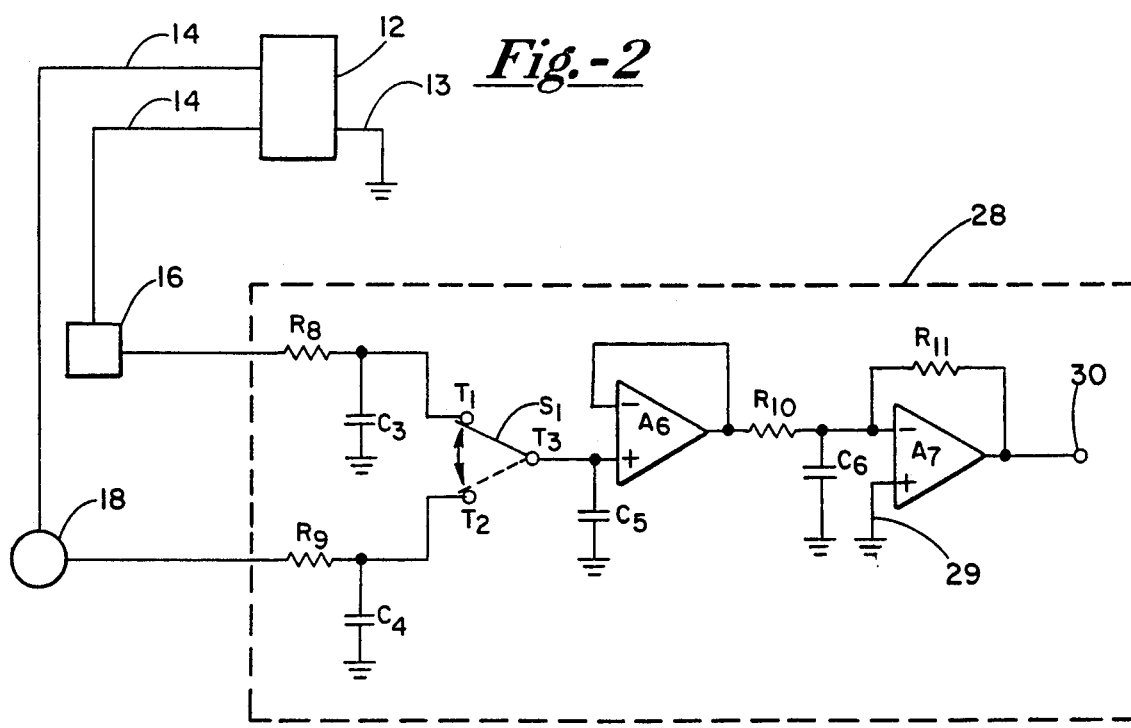
FIG. 2 illustrates a sampled data processing circuit according to an alternate embodiment of the invention for alternately sampling the electrical signals from the tip and ring electrode, wherein the operational amplifier buffers the signals and filters high frequency components.

Now referring to FIG. 2, a sampled data embodiment of the present invention is illustrated. Circuit 28 serves the same purpose as circuit 10 shown in FIG. 1, however, the signal processing is sampled data rather than in continuous time fashion. Circuit 28 also resides within the can of pacemaker 12, and is coupled to electrodes 14 internal to the pacemaker. However, for illustration purposes, circuit 28 is shown as residing exterior of the can 12 and coupled to the respective electrodes.

Series resistor $R_8$ is coupled to ring electrode 16. Similarly, series resistor $R_9$ is tied to tip electrode 18. A pair of shunt capacitors $C_3$ and $C_4$ are connected to respective resistors $R_8$ and $R_9$, and filter high frequency components to ground. Series resistor $R_8$ couples the sensed evoked ECG signal from ring electrode 16, as well as the residual potential, to terminal $T_1$ of a switch $S_1$. Switch $S_1$ is switched at a fixed frequency, typically 4 Khz, but which may be adjustable. Similarly, series resistor $R_9$ couples the sensed evoked ECG signal, as well as the residual potential on tip electrode 18, to terminal $T_2$ of switch $S_1$. In effect, switch $S_1$ alternately samples the electrical signals obtained from ring electrode 16 and tip electrode 18. Terminal $T_3$ of switch $S_1$ is connected to the positive input of amplifier $A_6$. Amplifier $A_6$ is a unity gain non-inverting operational amplifier which serves as an impedance buffer to subsequent inverting amplifier $A_7$. A shunt capacitor $C_5$ is provided at the positive input of amplifier $A_6$ to remove any high frequency components which may be generated by switch $S_1$.

Amplifier $A_7$ is provided in a low pass filter arrangement. An input resistor $R_{10}$ and shunt capacitor $C_6$ provide a single-pole RC low-pass filter, ideally designed to have a corner frequency of 100 hertz. The low-pass filter filters high frequency components, and also serves to average the electrical signals, which are alternately obtained from electrodes 16 and 18 by switch $S_1$. A resistor $R_1$ sets the gain of the output stage to the desired level. Thus, amplifier $A_7$, in effect, converts a non-continuous wave form, due to the 4 Khz switching frequency, to a smoothed signal at output terminal 30.

The low-pass filter realized by the arrangement of $A_7$ also provides an adding function to cancel out the residual potentials which are sensed at ring electrode 16 and tip electrode 18, similar to the summing arrangement of amplifier $A_5$ shown in FIG. 1. In this embodiment, again, the opposite polarized residual potentials will in effect be canceled. And again, a commonly sensed evoked ECG signal, which is a low frequency signal, will pass through amplifier $A_7$ to terminal 30. Subsequent classic R-waved detection circuits used for obtaining the evoked QRS complex can be coupled to output 30. However, digital R-wave detection circuits are also suited to process the outputted evoked ECG signal provided at terminal 30.

The ground reference 29 of circuit 28 is common to the ground reference 13, which is the outer can of pacemaker 12. However, the ground reference of circuit 28 need not be tied to can 12. It can be at a separate reference potential isolated from the can of pacemaker 12. Again, it is only important a third reference electrode electrically coupled to body tissues be provided in addition to the ring and tip electrode, and that the respective ring and tip signals be developed with respect to the reference electrode.

Referring to FIG. 3, an offset substraction circuit is shown which is suitable to either circuit 10 or 28. Terminal 32 is adapted to receive the outputted signal from either output terminal 24 or 30, and is connected to the negative input of differential amplifier $A_8$. A switch $S_2$ is connected between terminal 32 and the inverting input of differential amplifier $A_8$. A capacitor $C_7$ is connected between the inverting input of amplifier $A_8$ and the circuit ground to provide a classic sample and hold circuit. In the present invention, the signal from outputs 24 and 30 is sampled at the beginning of the detection window by briefly closing switch $S_2$. The outputted signal from terminal 34 serves as the zero reference and is subtracted in well known ways from all subsequently obtained signals from terminals 24 and 28, and the net signal is sent to the threshold detection circuitry. Thus, the signal is effectively reset to zero at the beginning of the detection window, and only changes in the obtained signal, such as those created by an evoked response, will exceed a typical threshold level. Any offset is thus removed from the circuitry prior to threshold sensing.

Now referring to FIG. 4, an alternative embodiment is illustrated implementing a unipolar pacing lead. A pacemaker, generally shown at 40, includes a housing defined by a conductive can, typically comprised of titanium, shown at 42. Can 42 is electrically partitioned wherein a majority of the can serves as the second electrode, as illustrated at 44. A reference button-shaped electrode 46 forms a separate portion of can 42 and is electrically isolated from the remaining portion of the can 44 serving as the second electrode. An electrically non-conductive strip 48 of can 42 separates the reference electrode 46 from second electrode 44. A unipolar cardiac pacing lead 50 communicates a generated electrical stimulus pulse from pacing electronics of pacemaker 40 to a tip and first electrode 52 at a distal end thereof. In this embodiment, second electrode 44, which forms a portion of pacemaker can 42, serves as the anode and is functionally equivalent to the ring electrode of a bipolar lead shown in FIG. 1. The tip electrode 52 serves as the cathode. During use, tip electrode 52 is positioned within a chamber of the heart, and is remotely located from second electrode 44.

In operation, a pacing pulse is applied by the pacing electronics to both tip electrode 52 and second electrode 44 in reference to reference electrode 46, which is electrically coupled to body tissues. Subsequently, the evoked ECG signal can be obtained from tip electrode 52 and second electrode 46 using the signal processing circuitry 10 or 28 shown in FIGS. 1 and 2, wherein a first unipolar signal is obtained from tip electrode 52, and a second unipolar signal is obtained from second electrode 44, wherein each signal is obtained in reference to reference electrode 46. Hence, the present invention can be implemented using either a bipolar or unipolar pacing lead.

In still yet another embodiment, second electrode 44 can be provided as a separate unipolar pacing lead, similar to lead 50, and having a second electrode at a distal end similar to first electrode 52. Thus, the second electrode could be selectively located more proximate to first electrode 52 as desired. In this embodiment, circuitry 10 or 28 is coupled to each of the distal electrodes via the unipolar leads for subsequent signal processing, as previously described, wherein a first and second signal would be obtained in a unipolar mode in reference to reference electrode 46, which could be the entire pacemaker can 42 in this embodiment.

It is noted that the present invention facilitates sensing the evoked ECG signal. Such detection can be used using other devices, such as external Pacing System Analyzers which may or may not generate the pacing stimulus pulse. Thus, limitation to devices which actually generate the electrical stimulus pulse, or to devices which are implantable, is not to be inferred. Rather, the present invention is generally directed to a signal processing circuit which can be coupled to a pair of electrodes for obtaining the evoked ECG signal using summation techniques. Hence, the present invention is generally directed towards analysis, and can be implemented in implantable cardiac pacemaker, or in analyzing equipment.

OPERATION

In operation, the evoked ECG signal is obtained by either circuit 10 or 28 during a post-pacing predetermined time window, preferably, 10 to 60 milliseconds after application of the electrical stimulus pulse. A$_3$ is well known is the field of cardiac pacing, the recharge cycle defines the period (typically 20-30 milliseconds) of time following the issue of the pacing pulse when the pacing output capacitor is recharged. Pacing systems must be capacitively coupled so as to deliver no long term net charge. In some designs, a capacitor is, instead, charged through the heart during the pacing pulse, in which case the ensuing cycle might be referred to as a discharge cycle. For the present invention, either technique is equivalent, and the term "recharge" will be adhered to. The recharge current thus flows in the opposite direction to the pacing current, and has a dissipating effect on the polarization potentials on each electrode. However, attempting to sense an evoked response concurrent with the recharge cycle is not desirable, as this introduces further dynamics at each electrode. A preferred approach is to interrupt normal recharge after a predetermined short interval, typically 3 milliseconds, and allow a predetermined settling time, typically 7 millisecond, before looking for an evoked response at the output of the previously described summing circuit. Thus, the large polarization voltages on each electrode are somewhat dissipated during the short 3 milliseconds period, but the electrodes are allowed to stabilize during the short 7 millisecond period before detection begins. The sense window thus typically extends from 10 milliseconds post pacing to 60 milliseconds. At the end of the detection window the balance of the recharge cycle can be completed.

The time of interruption before the 10-60 millisecond window is programmable by the physician at the time of implantation, or remotely set using appropriate remote control devices. This feature is referred to as variable or dynamic recharge interruption. In the prior art, to avoid the sense amplifiers from being blind during this recharge period, the recharge cycle is shortened to less than 10 milliseconds by actively reversing the voltage polarity on the ring and tip electrodes. Though active recharge would work as a complement to this invention, the energy disadvantages of this opposite going secondary phase have been discussed. The present invention implements an interruption of a passive recharge cycle at some point 0 to 10 milliseconds post pace. The pacer output capacitor is transitorily disconnected, and the evoked ECG response sense amplifier circuit 10 is utilized by the pacer electronics for typically 50 to 100 milliseconds. This window ensures the electronics has a suitable "look period" for the evoked response. Then the output capacitor may then be switched back in to complete the recharge cycle. Thus, the sensing and signal processing scheme takes place without the added artifact that the pacer output capacitor recharge event would have introduced.

An offset removal technique implemented at the beginning of the detection window is advantageous, particularly if the detection is to be accomplished by classic threshold techniques. In these classic methods, the absolute value of the summed signal is compared with a threshold level, and if said threshold level is exceeded, detection has occurred. The offset removal technique disclosed herein is applicable to the output of either circuit 10 or circuit 28. In this technique, the summed signal value at the beginning of the detection window is sampled to obtain a zero reference. This zero reference is then subtracted from the subsequently obtained signals throughout the detection window. Thus, the output signal is effectively reset to zero at the beginning of the detection window, and only changes in the signal, such as those from an evoked response, will exceed a typical predetermined threshold level. The offset is thus removed.

In summary, the present invention obtains and processes electrical signals which are sensed by the ring and tip electrode of a typical pacemaker bipolar lead. The circuit senses each of these signals from the ring tip electrode in a unipolar mode. The sensed electrical signals are subsequently added to cancel or null the opposing residual potentials which remain on the ring and tip electrode post pacing. Thus, since the circuit is adding the signals, the common-potential evoked ECG signal is added and presented for subsequent detection of the QRS complex. The higher level residual potential signals are removed prior to the subsequent signal processing, and the low level ECG signal is retained. Thus, the circuit facilitate automatic capture techniques of the evoked ECG signal. The circuits can be implemented in either an analog or digital format, as disclosed. While the signal processing weighting functions provided forward of the summing circuitry is desirable to normalize the signals, it is not required. Hence, the present invention sets forth an apparatus and method of adding the signals, rather than processing the signals in a differential mode. Further, the generation of a biphasic or tripbasic pace pulse to quickly eliminate polarization by active processing is not required. Hence, the power requirements the circuits according to the present invention is reduced over the prior art, and the battery life of the pacemaker is increased. The 20 to 30 millisecond natural charging cycle is merely interrupted to sense the evoked ECG signal, and the charging is done passively using the normal recharge feature through the heart ventricle. Again, power requirements are reduced.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

We claim:

1. An apparatus for cardiac pacing and sensing, comprising:
   (a) a bipolar cardiac pacing lead adapted for positioning within a heart chamber, said lead having a distal end with a first electrode, and a second electrode spaced from said first electrode;
   (b) a reference electrode electrically isolated from both first and second electrodes;
   (c) means for transmitting to both said first and second electrode an electrical stimulus pulse in a bipolar mode; and
   (d) circuit means connected to both said first and second electrodes and said reference electrode for obtaining an evoked electrical potential, said circuit means comprising first means for sensing a first electrical signal at said first electrode in a unipolar mode in reference to said reference electrode, second means for sensing a second electrical signal at said second electrode in a unipolar mode in reference to said reference electrode, and means for adding said first and second signals from said first and second sensing means to cancel out any residual opposite polarized potentials and to obtain the evoked electrical potential.

2. The apparatus as specified in claim 1 wherein said transmitting means further comprises means for discharging polarization from said first and second electrodes, wherein said transmitting means comprises interruption means for momentarily interrupting said discharging means from discharging polarization from said first and second electrodes.

3. The apparatus as specified in claim 1 wherein said first sensing means further comprises a first time domain adjusting means for adjusting an exponential decay of said first electrical signal.

4. The apparatus as specified in claim 3 wherein said second sensing means further comprises a second time domain adjusting means for adjusting an exponential decay rate of said second electrical signal.

5. The apparatus as specified in claim 3 wherein said first time domain adjusting means comprises a low-pass filter having an operational amplifier, a resistor and a variable capacitor.

6. The apparatus as specified in claim 1 wherein said first sensing means further comprises a first amplitude adjusting means for adjusting an amplitude of said first electrical signal.

7. The apparatus as specified in claim 6 wherein said second sensing means further comprises a second amplitude adjusting means for adjusting an amplitude of said second electrical signal.

8. The apparatus as specified in claim 6 wherein said first sensing means further comprises a first amplifier for amplifying said first electrical signal.

9. The apparatus as specified in claim 8 wherein said second sensing means further comprises a second amplifier for amplifying said second electrical signal.

10. The apparatus as specified in claim 6 wherein said first amplitude adjusting means comprises a low-pass filter having an operational amplifier and a variable feedback resistor for adjusting a gain of said amplifier.

11. The apparatus as specified in claim 1 wherein said adding means of said circuit means comprises an operational amplifier having a first input connected to both first and second sensing means to add both first and second electrical signals, and an output for outputting said evoked electrical potential.

12. The apparatus as specified in claim 1 wherein said circuit means comprises digital signal processing means for obtaining said evoked electrical potential.

13. The apparatus as specified in claim 1 wherein said circuit means comprises an analog sampling data circuit which alternately samples said first and second electrical signals.

14. The apparatus as specified in claim 1 further comprising offset removal means connected to said adding means for removing an offset from said obtained evoked electrical potential.

15. An apparatus for cardiac pacing and sensing, comprising:
   (a) a unipolar cardiac pacing lead adapted for positioning within a heart chamber, said lead having a distal end with a first electrode;
   (b) a second electrode and a reference electrode each electrically isolated from said first electrode and each other;
   (c) means for transmitting to both said first and second electrode an electrical stimulus pulse; and
   (d) circuit means connected to both said first and second electrodes and said reference electrode for obtaining an evoked electrical potential, said circuit means comprising first means for sensing a first electrical signal at said first electrode in a unipolar mode in reference to said reference electrode, second means for sensing a second electrical signal at said second electrode in a unipolar mode in reference to said reference electrode, and means for adding said first and second signals from said first and second sensing means to cancel out any residual opposite polarized potentials and to obtain the evoked electrical potential.

16. The apparatus as specified in claim 15 wherein said second electrode is remotely positionable from said first electrode.

17. The apparatus as specified in claim 16 further having a housing encasing said circuit means, wherein a first portion of said housing forms said second electrode, and a second portion of said housing electrically isolated from said first portion forms said reference electrode.

18. An apparatus for obtaining an evoked electrical potential, comprising:
   (a) a first electrode adapted to be positioned within a heart chamber;
   (b) a second electrode adapted to be located proximate the heart chamber and electrically isolated from said first electrode;
   (c) a reference electrode electrically isolated from both first and second electrodes; and
   (d) circuit means connected to both said first and second electrodes and said reference electrode for obtaining the evoked electrical potential, said circuit means comprising first means for sensing a first electrical signal at said first electrode in a unipolar mode in reference to said reference electrode, second means for sensing a second electrical signal at said second electrode in a unipolar mode in reference to said reference electrode, and means for adding said first and second signals from said first and second sensing means to cancel out any residual opposite polarized potentials on said first and second electrodes and to obtain the evoked electrical potential.

19. A method of pacing a heart and obtaining an evoked ECG signal, comprising the steps of:
   (a) applying an electrical stimulus pulse to said heart via an electrically isolated first and second electrode;
   (b) sensing a first electrical signal at said first electrode in a unipolar mode in reference to a reference electrode which is electrically isolated from said first and second electrodes;
   (c) sensing a second electrical signal at said second electrode in a unipolar mode in reference to said reference electrode; and
   (d) adding said first and second signal to cancel any oppositely polarized potentials on said first and second electrodes and to obtain a third signal including the evoked ECG signal from said heart.

20. The method of claim 19 further comprising the step of adjusting an exponential decay rate of the first signal before adding with said second signal.

21. The method of claim 20 further comprising the step of adjusting an exponential decay rate of the second signal before adding with said first signal.

22. The method of claim 19 further comprising the step of adjusting an amplitude of said first signal before adding with said second signal.

23. The method of claim 22 further comprising the step of adjusting the amplitude of the second signal before adding with the first signal.

24. The method of claim 19 further comprising the step of interrupting a discharging of polarization from said first and second electrodes while adding said first and second signals.

25. The method of claim 24 further comprising the step of interrupting a discharging of polarization from said first and second electrodes a preselected time period after applying said electrical stimulus pulse.

26. The method of claim 19 further comprising the step of adding said first and second signals immediately after applying said electrical stimulus pulse to obtain an offset reference signal, then subsequently substracting obtained said third signals from said offset reference signal to obtain a normalized signal.

27. The method of claim 24 further comprising the step of performing step (d) a predetermined time period after interrupting discharging said first and second electrodes.

28. The method of claim 19 further comprising the step of providing a bipolar pacing lead in step (a) wherein said first and second electrodes are defined by a ring and tip electrode.

29. The method of claim 19 further comprising the step of providing a unipolar lead in step (a) having said first electrode.

30. The method of claim 29 further comprising the step of remotely positioning said second electrode from said first electrode in step (a).

31. A method of obtaining an evoked ECG signal from a heart comprising the steps of:
   (a) sensing a first and second electrical signal at a respective electrically isolated first and second electrode, wherein each said signal is obtained in reference to a reference electrode which is electrically isolated from both said first and second electrodes, wherein at least one said first or second electrode is positioned within a heart chamber; and
   (b) adding said first and second signal to cancel any oppositely polarized potentials on said first and second electrodes, and to obtain a third signal including the evoked ECG signal from the heart.

* * * * *